US009901752B2

United States Patent
Piret (10) Patent No.: US 9,901,752 B2
(45) Date of Patent: Feb. 27, 2018

(54) HADRON THERAPY INSTALLATION WITH MOVING FLOOR

(71) Applicant: ION BEAM APPLICATIONS S.A., Louvain-la-Neuve (BE)

(72) Inventor: Vincent Piret, Gembloux (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 343 days.

(21) Appl. No.: 14/426,892

(22) PCT Filed: Sep. 10, 2013

(86) PCT No.: PCT/EP2013/068762
§ 371 (c)(1),
(2) Date: Mar. 9, 2015

(87) PCT Pub. No.: WO2014/041003
PCT Pub. Date: Mar. 20, 2014

(65) Prior Publication Data
US 2015/0231412 A1    Aug. 20, 2015

Related U.S. Application Data

(60) Provisional application No. 61/700,694, filed on Sep. 13, 2012.

(30) Foreign Application Priority Data

Sep. 11, 2012   (BE) .................................. 2012/0605

(51) Int. Cl.
*A61N 5/10*   (2006.01)

(52) U.S. Cl.
CPC ......... *A61N 5/1081* (2013.01); *A61N 5/1048* (2013.01); *A61N 2005/1085* (2013.01)

(58) Field of Classification Search
CPC .......... A61N 5/1081; A61N 2005/1085; A61N 5/1048
See application file for complete search history.

(56) References Cited

U.S. PATENT DOCUMENTS

2011/0299657 A1* 12/2011 Havelange ........... A61N 5/1081
378/65

* cited by examiner

*Primary Examiner* — Christine H Matthews
*Assistant Examiner* — Joshua D Lannu
(74) *Attorney, Agent, or Firm* — Finnegan, Henderson, Farabow, Garrett & Dunner LLP (57) ABSTRACT

The present disclosure relates to a hadron therapy installation comprising a moving floor in the form of a deformable band guided in a guide structure. The moving floor comprises a lower segment and an upper segment. The lower segment can be pulled by the irradiation unit from a lower docked position to a position in which the lower segment forms a substantially horizontal floor surface when the irradiation unit is in a first angular position. The upper segment can be pulled by the irradiation unit from an upper docked position to a position in which the upper segment at least partially forms the substantially horizontal floor surface when the irradiation unit is in a second angular position. The lower segment and the upper segment may have a finite length and a counterweight further connected to the free end of the upper segment.

23 Claims, 7 Drawing Sheets

HADRON THERAPY INSTALLATION WITH MOVING FLOOR

TECHNICAL FIELD

The present invention relates to a hadron therapy installation with a moving floor.

BACKGROUND OF THE INVENTION

Recent hadron therapy techniques for treating cancers make it possible to deliver a dose precisely on a target volume, for example a tumor, while preserving the surrounding tissue. A hadron therapy installation generally comprises a particle accelerator producing a beam of charged particles, a rotary gantry comprising transport means for the beam, and an irradiation unit. The irradiation unit delivers a dose distribution on the target volume and generally comprises means for monitoring the delivered dose, for example such as an ionization chamber, as well as means for monitoring the direction or shape of the beam.

The rotary gantry is capable of rotating about a horizontal axis of rotation, such that the irradiation unit can deliver a treatment beam at several irradiation angles. The rotary gantries of the traditional hadron therapy installations are generally designed to rotate 360° about a horizontal axis of rotation.

The rotary irradiation unit protrudes in a treatment chamber through a passage at least partially closed by a moving floor. This moving floor facilitates therapist access to the patient completely safely, while allowing the irradiation unit to rotate. Different models of moving floors have been developed.

Document U.S. Pat. No. 7,997,553 describes a hadron therapy installation comprising a rotary gantry that supports a beam transport line ending with an irradiation unit. A treatment chamber comprises a passage for the irradiation unit, which is covered at the floor of the treatment chamber by a moving floor. This floor comprises a plurality of moving panels positioned next to each other. During rotation of the gantry, each of these moving panels is actuated individually between a first position freeing the passage for an irradiation unit and a second position covering the passage around the irradiation unit. Such a floor requires means for monitoring the movement of a plurality of panels synchronously with the rotation of the gantry. These panels must be able to retract and extend in a short enough amount of time to avoid a collision between the irradiation unit and one of the panels on the one hand, and to avoid a risk of accident due to opening of the passage around the irradiation unit during an excessively long period of time on the other hand. Based on the angular position of the irradiation unit, an empty space may still exist between the irradiation unit and one of the panels of the four.

Document WO2010/076270 also describes a hadron therapy installation comprising a gantry that can rotate about a horizontal axis and supporting a beam transport line ending with an irradiation unit. A treatment chamber comprises a horizontal floor overhung by a cylindrical roof. The irradiation unit penetrates that treatment chamber through a transverse passage, which allows a 360° rotation of the irradiation unit about said horizontal axis. A moving floor closes said passage while forming a planar access surface at the floor of the treatment chamber, and a cylindrical separating wall at the roof. The proposed moving floor is made up of a main floor and two secondary floors each comprising a plurality of rigid transverse plates flexibly linked to each other. The main floor is driven by the gantry and the secondary floors are driven by the irradiation unit. The configuration of said moving floor completely closes the passage over 360° in any position of the irradiation unit. Other moving floor configurations are discussed in this same document, which is incorporated by reference into this application.

Document WO2010/076270 also describes a mechanism for connecting the secondary floors to the irradiation unit. This mechanism comprises two pairs of traction rails arranged on either side of the irradiation unit. Each of the two secondary floors comprises at least one pivot joint slidably guided in one of said pairs of traction rails. The pair of traction rails guides said pivot joint along a rectilinear path transverse to the direction of movement of the moving floor, and thus allows the moving floor to turn between the circular part and the straight part of the guide structure. Each of the traction rails is also part of a buffer mechanism that makes it possible to absorb a residual movement of the irradiation unit, when one of the secondary floors is accidentally immobilized. In a first embodiment, this buffer mechanism assumes the form of a deformable parallelogram comprising, for each rail, a member fastened to the irradiation unit, a member parallel to the rail, and a member parallel to the member fastened to the irradiation unit. The piston is connected between the traction rail and the member parallel to the traction rail. As long as the compression force transmitted by the piston remains below a threshold value, the piston forms a rigid transmission element. If the compression force transmitted by the piston exceeds the threshold value, the piston contracts and the deformable parallelogram is flattened, thus absorbing a residual movement of the irradiation unit when the floor connected to the deformable parallelogram is immobilized. In a second embodiment of this buffer mechanism, each end of a traction rail is connected to the irradiation unit by means of a piston. The buffer mechanism then comprises at least 4 pistons, preferably 8 pistons. The pistons comprise a load cell and are capable of contracting in case of immobilization of the moving floor to absorb a residual rotational movement of approximately 3° to 5° of the rotary gantry after an emergency stop command of the gantry transmitted by the load cell to the monitoring system of the hadron therapy installation. The present invention also aims to improve the connection of moving floor segments to the irradiation unit, in particular by reducing the number of mechanical parts around the irradiation unit, by freeing space around the irradiation unit to allow the placement of new accessories on the irradiation unit, and still further reducing the risk of immobilization of the moving floor in its guide structure.

The traditional hadron therapy installations require considerable space, and their on-site assembly is generally fairly labor-intensive. In order to reduce the costs related in particular to space constraints, new, more compact installations have been presented. The document "Gantries" by E. Pedroni Center for Proton Radiation Therapy—Paul Scherrer Institute—WE Chiba Jan. 5, 2010, describes most of the hadron therapy installations comprised in the state of the art, as well as a more compact installation developed by PSI and called "PSI Gantry 2". This installation comprises a rotary gantry whereof the rotation about the horizontal axis of rotation is limited between two extreme angular positions of −30° and +180°. These angles are measured relative to a vertical plane comprising the axis of rotation, where an angle of 0° corresponds to the angular position in which the delivery line of the beam is at its highest position. (This convention for measuring angular positions of the rotary gantry and/or the irradiation unit supported by said rotary gantry will be maintained hereafter.)

Document EP 2308561 A1 describes another compact hadron therapy installation comprising a rotary gantry capable of rotating about a horizontal axis of rotation between two extreme angular positions of −35° and +190°.

These compact hadron therapy installations with an amplitude of rotation much lower than 360° must also be equipped with a floor, both for safety reasons and for accessibility reasons with respect to the patient. The known moving floors of the traditional hadron therapy installations (with an amplitude of rotation of 360°) could also be implemented on a compact hadron therapy installation. It is, however, more advantageous to use a floor system offering easier access around the patient, for example allowing the introduction of imaging means or means for monitoring the position of the patient.

Document U.S. Pat. No. 7,348,579 describes a hadron therapy installation whereof the gantry is capable of rotating about a horizontal axis of rotation between two angular positions comprised between 0° and 180°. The installation comprises a treatment chamber with a passage for the irradiation unit and a device capable of covering the passage irrespective of the position of the irradiation unit.

The filer of this application recently announced the launch of a smaller proton therapy system allowing lateral access to the treatment chamber. This installation comprises a rotary gantry capable of rotating about a horizontal axis of rotation between two angular positions comprised between −30° and 190°. For this very compact installation, a treatment floor is developed in the form of a deformable band guided in a guide structure that requires a reduced installation volume. However, for such a compact moving floor solution, the risk of immobilization of the moving floor is particularly high.

Consequently, the first problem at the base of the present invention is to propose a hadron therapy installation comprising: an irradiation unit with a horizontal axis of rotation capable of rotating around a treatment area between a first angular position (α), situated above the treatment area, and a second angular position (β), situated below said treatment area; and moving floor in the form of a deformable band guided in a guide structure, which requires a reduced installation volume, provides excellent access to the patient, and has a relatively low risk of immobilization.

BRIEF DESCRIPTION OF THE INVENTION

According to a first aspect of the invention, a hadron therapy installation that comprises: an irradiation unit with a horizontal axis of rotation capable of rotating around the treatment area between a first angular position (α), situated above the treatment area, and a second angular position (β), situated below the treatment area; a moving floor in the form of a band deformable in the longitudinal direction, comprising a lower segment and an upper segment situated on either side of the irradiation unit; a guide structure guiding the moving floor along a path around the treatment area such that it forms a substantially horizontal floor surface below the treatment area and a wall surrounding the treatment area as far as the first angular position above the floor surface, so as preferably to allow a lateral access bay to exist toward the treatment area. The lower segment can be pulled by the irradiation unit from a lower docked position, in which it is found when the irradiation unit is in the second angular position, to a final operational position, in which it is found when the irradiation unit is in the first angular position, and in which it forms the substantially horizontal floor surface.

The upper segment can be pulled by the irradiation unit from an upper docked position, in which it is found when the irradiation unit is in the first angular position, to a final operational position, in which it is found when the irradiation unit is in its second angular position, and in which it at least partially forms the substantially horizontal floor surface. The lower segment and the upper segment are segments with a finite length, each comprising a free end. A traction device is connected to the free end of the upper segment, so as to exert a traction force on the upper segment toward the upper docked position sufficient to keep the upper segment under axial tension independent from the angular position and direction of movement of the irradiation unit. By keeping the upper segment under constant axial tension, over the entire length thereof and independently of the angular position and the direction of movement of the irradiation unit, the risk of that upper segment immobilizing the guide structure is substantially reduced. This is particularly true if the moving floor for example comprises a plurality of transverse segments articulated to each other. It will also be understood that the traction force also at least partially compensates the force exerted by the weight of the lower segment 8' on the irradiation unit and thereby discharges the latter at least partially. It follows that the motor for rotating the rotary gantry supporting the irradiation unit may be smaller, and that imprecisions in the angular positioning of the irradiation unit, possibly due to a deformation of the rotary gantry under a load, are less significant.

The traction device may for example be a rotary or linear electric, hydraulic, pneumatic or spring motor controlled so as to exert a traction force, either directly or via a chain, cable or band, toward the upper docked position that is sufficient to keep the upper segment under axial tension, independently of the angular position and the direction of movement of the irradiation unit. In one preferred, particularly simple, reliable and compact embodiment, the traction device comprises a counterweight that is connected to the free end of the upper segment.

A similar traction device could also be connected to the free end of the lower segment, so as to exert a traction force on that lower segment toward the lower docked position. Most often, however, the weight of the lower segment itself is sufficient to keep the latter under axial tension, such that a counterweight for the lower segment is most often not necessary.

According to one particularly simple and compact preferred embodiment, a counterweight is connected to the upper segment by at least one cable guided by at least one pulley. The cable/pulley guiding system in particular makes it possible to choose the location of the counterweight completely freely, even outside the location where the guide structure with the moving floor is located. It should be noted that a rope, chain or strip are to be considered technical equivalents of a "cable" and static guide elements are to be considered technical equivalents of a "pulley".

To make the installation particularly compact and to avoid hindering lateral access to the treatment area, the end portion of the upper segment is advantageously arranged above the irradiation unit, if the upper segment is completely arranged in the upper docked position.

In this upper docked position, the upper segment advantageously forms an open loop, and the end portion of the upper segment is preferably arranged in a plane extending above the irradiation unit. This arrangement is very compact, and the open loop ensures reliable movement of the upper segment under the traction force exerted by the counterweight.

Similarly, the end part of the lower segment is advantageously arranged below the irradiation unit, if the lower segment is arranged in the lower docked position. In this lower docked position, the lower segment advantageously forms an open loop, and the end portion of the lower segment is preferably arranged in a plane extending below the irradiation unit. This arrangement is very compact, and the open loop also ensures reliable movement of the lower segment under the effect of its own weight, if applicable, assisted by a counterweight.

The guide structure generally comprises guide rails. The latter preferably comprise: a first portion, capable of guiding the moving floor along a linear path to form the planar and substantially horizontal floor surface below the treatment area; a second portion, capable of guiding the moving floor along a path in the shape of an arc of circle to form, above the planar floor surface, a surface in the shape of a cylinder segment that surrounds the treatment area as far as the first angular position ($\alpha$), so as preferably to allow a lateral access bay toward the treatment area to remain; a third portion, which extends the first portion downward, and is preferably capable of guiding the lower segment along a path in the form of an open loop, to form the lower docked position for the lower segment; and a fourth portion, which extends the second portion upward, which is preferably capable of guiding the lower segment along a path in the shape of an open loop, to form the upper docked position for the upper segment.

In one advantageous embodiment, a rigid traction frame surrounds the irradiation unit with functional play on either side thereof and supported by the irradiation unit such that the rotating irradiation unit can move relative to the traction frame within the limit of said functional play. The segments of the floor are connected on either side of the rigid traction frame. Force transmitting means are arranged between the traction frame and the irradiation unit so as to immobilize the traction frame in a central position relative to the irradiation unit, as long as the force transmitted by the force transmitting means remains below a threshold value. The force transmitting means comprise at least one safety element that gives way when the transmitted force exceeds said threshold value, to allow relative movement of the irradiation unit with respect to the traction frame while taking advantage of such functional play. It will be understood that this mechanism improves the connection of the floor segments to the irradiation unit, for example by reducing the number of mechanical parts around the irradiation unit and thus freeing up space around the irradiation unit, in particular to allow the placement of new accessories on the irradiation unit.

Preferably, the solution described in the preceding paragraph further comprises a detection device capable of detecting that the safety element has given way and a monitoring system capable of activating an emergency stop of the rotation of said irradiation unit when the detection device detects that the safety element has given way.

In one preferred embodiment, the traction frame is supported by the irradiation unit by means of two suspension arms, so as to form a mechanism with four articulations arranged at the four corners of a parallelogram.

In one preferred embodiment, as it is very simple and still very reliable, the force transmitting means comprise at least one telescoping element, the extension and shortening of which are blocked by at least one stop key. The stop key then forms said safety element, which gives way when the transmitted force exceeds said threshold value.

To avoid seriously damaging the irradiation unit and/or the moving floor in case of immobilization of the latter, the connection between the traction frame and the irradiation unit is advantageously designed to break at predefined rupture points in case of immobilization of the floor.

The connection between the irradiation unit and the lower segment advantageously comprises a pivot joint and a traction rail, said traction rail guiding the pivot joint along a trajectory defined to optimize the transmission of a traction force from the traction frame on the lower segment. Similarly, the connection between the traction frame and the upper segment advantageously comprises a pivot joint and a traction rail, said traction rail guiding the pivot joint along a trajectory defined to optimize the transmission of a traction force from the traction frame on the upper segment. It will be understood that the solution also contributes to reducing the risk of immobilization of the moving floor in the guide structure. It should also be noted that in one preferred embodiment, the traction rail defines a substantially linear trajectory portion, followed by a rounded convex trajectory portion.

Preferably, the installation also comprises a laser source capable of producing a laser beam for positioning a patient. The laser source is then advantageously positioned on a support behind the moving floor, and at least one of the floor segments comprises an opening for the passage of the laser beam.

The installation may further also comprise an imaging device. This imaging device preferably comprises at least one x-ray tube and an x-ray detection panel that are situated on either side of the moving floor.

In one preferred embodiment, the moving floor comprises a plurality of transverse segments that are articulated to each other such that the moving floor can follow the path defined by the guide structure.

If the four quadrants defined by a vertical plane (A', A") and a horizontal plane (B', B") both containing the axis of rotation are numbered as follows: the first quadrant and the second quadrant are located next to one another above the horizontal plane (B', B"); the third quadrant is located below the second quadrant; and the fourth quadrant is located below the first quadrant; then, in the first angular position ($\alpha$), the irradiation unit is arranged in the first quadrant; and in its second angular position ($\beta$), the irradiation unit is arranged either at the boundary of the third and fourth quadrants, or in the fourth quadrant.

According to another aspect, the invention relates to a hadron therapy installation comprising: an irradiation unit with a horizontal axis of rotation capable of rotating around a treatment area; a moving floor in the form of a band deformable in the longitudinal direction and guided in a guide structure, comprising a segment on either side of the irradiation unit; and a traction mechanism arranged between the irradiation unit and the two segments of the moving floor, such that the irradiation unit can drive the floor segments via that traction mechanism that rotates about its axis of rotation. This traction mechanism comprises: a rigid traction frame surrounding the irradiation unit with functional play on either side thereof and supported by the irradiation unit such that the rotating irradiation unit can move relative to the traction frame within the limits of said functional play. The segments of the floor are connected on either side of the rigid traction frame. Force transmitting means are arranged between the traction frame and the irradiation unit so as to freeze the traction frame in a central position relative to the irradiation unit, as long as the force transmitted by the force transmitting means remains below a threshold value. These force transmitting means comprise at least one safety element that gives way when the transmitted force exceeds said threshold value, to allow a relative movement of the irradiation unit with respect to said traction frame while taking advantage of said functional play. It will be understood that this mechanism generally improves the connection of moving floors to the irradiation unit, for example by reducing the number of mechanical parts around the irradiation unit and thus freeing up space around the irradiation unit, in particular to allow the placement of new accessories on the irradiation unit.

Preferably, the installation described in the preceding paragraph further comprises a detection device capable of detecting that the safety element has given way and a monitoring system capable of activating an emergency stop of the rotation of said irradiation unit when the detection device detects that the safety element has given way.

In one preferred embodiment, the traction frame is supported by the irradiation unit by means of two suspension arms, so as to form a mechanism with four articulations arranged in the four corners of a parallelogram.

In one preferred embodiment, as it is very simple and still very reliable, the force transmitting means comprise at least one telescoping element, the extension and shortening of which are blocked by at least one stop key. This stop key then forms said safety element, which gives way when the transmitted force exceeds said threshold value.

The connection between the traction frame and the lower segment advantageously comprises a pivot joint and a traction rail, said traction rail guiding the pivot joint along a trajectory defined to optimize the transmission of a traction force from the traction frame on the lower segment. Similarly, the connection between the traction frame and the upper segment advantageously comprises a pivot joint and a traction rail, said traction rail guiding the pivot joint along a trajectory defined to optimize the transmission of a traction force from the traction frame on the upper segment. It will be understood that this solution also contributes to reducing the risk of immobilization of the moving floor in the guide structure. It should also be noted that in one preferred embodiment, the traction rail defines a trajectory portion that is substantially linear, followed by a rounded convex trajectory portion.

BRIEF DESCRIPTION OF THE DRAWINGS

To better understand the invention and its advantages, one preferred embodiment and several alternative embodiments thereof are described below as an illustration and non-limitingly, in reference to the appended drawings, in which.

DETAILED DESCRIPTION OF THE INVENTION

Figure 1:
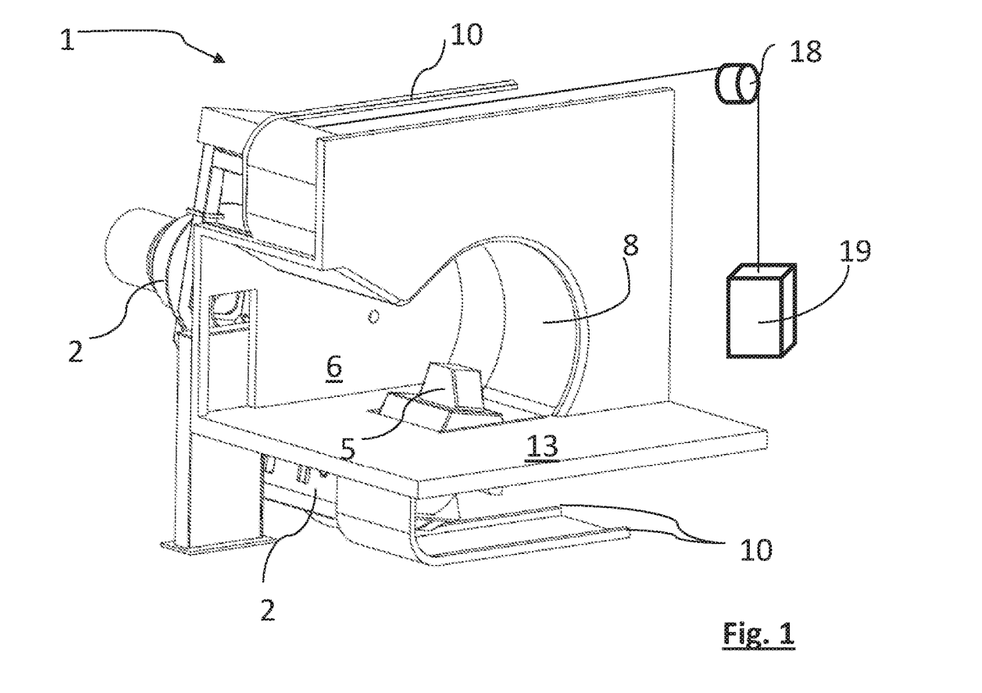
FIG. 1: is a simplified three-dimensional view of a hadron therapy installation according to the present invention with an irradiation unit with a horizontal axis of rotation.

FIG. 1 shows a hadron therapy installation 1. Such an installation generally comprises an isocentric rotary gantry 2 (not shown). This gantry 2 is capable of rotating about a horizontal axis of rotation 3. The gantry 2 supports a beam transport line (not shown) and an irradiation unit 5 capable of delivering a beam substantially perpendicular to said horizontal axis of rotation 3. The rotary irradiation unit 5 protrudes in a treatment chamber 6 through a passage closed by a moving floor 8.

Figure 2:
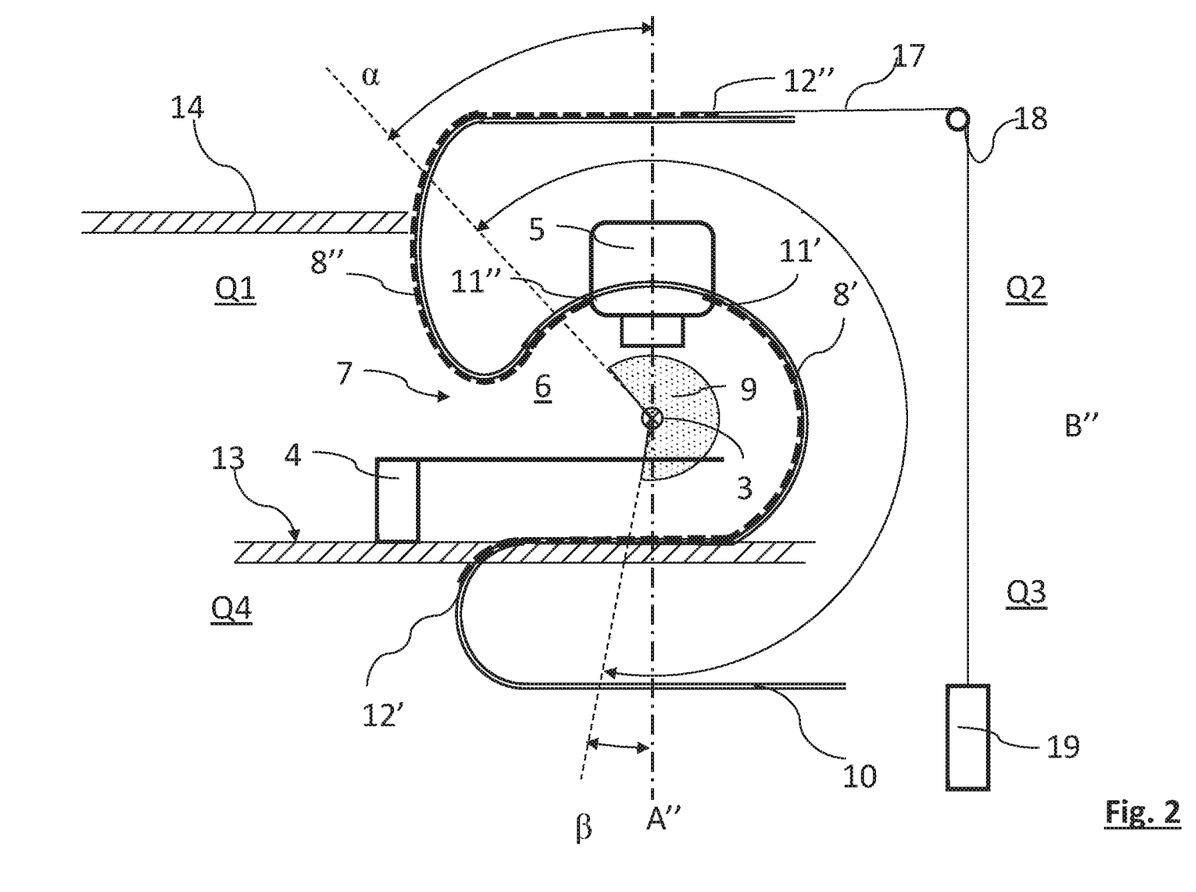
FIG. 2: is a simplified cross-section of the hadron therapy installation according to FIG. 1, the cutting plane being perpendicular to the axis of rotation of the irradiation unit.

FIG. 2 shows a simplified cross-section of the hadron therapy installation according to FIG. 1, the cutting plane being perpendicular to the axis of rotation 3 of the irradiation unit 5. The gantry 2 is capable of rotating about the horizontal axis of rotation 3 between a first angular position $\alpha$ and a second angular position $\beta$, around the treatment area 9. These angles $\alpha$ and $\beta$ are measured relative to a vertical plane A'A" comprising the horizontal axis of rotation 3, $\alpha$ preferably being comprised between $-15°$ and $-45°$, and $\beta$ preferably being comprised between $+180°$ and $+200°$, an angle of $0°$ corresponding to the position in which the irradiation unit 5 is located in its uppermost position. In FIG. 2, the irradiation unit is for example capable of rotating around a horizontal axis between two angular positions comprised between $\alpha=-45°$ and $\beta=+190°$. In other words, if Q1, Q2, Q3 and Q4 designate the four quadrants defined by a horizontal plane (B', B") and the vertical plane (A', A") both containing the axis of rotation 2, as indicated in FIG. 2, then in its first angular position $\alpha$, the irradiation unit is arranged in the first quadrant Q1; and in the second angular position $\beta$, the irradiation unit is arranged either at the boundary of the third quadrant Q3 and the fourth quadrant Q4, or completely in the fourth quadrant Q4. More generally, the irradiation unit 5 can then rotate around a treatment area 9, between a first angular position $\alpha$, situated above the treatment area 9, and a second angular position $\beta$, situated below the treatment area 9.

The isocentric gantry may for example be a gantry as described in patent EP 2308561 B1 and currently unpublished patent application EP 12167394.1, which are incorporated by reference.

The moving floor 8 is designed in the form of a band deformable in the longitudinal direction. It comprises a lower segment 8' and an upper segment 8" situated on either side of the irradiation unit 5. A guide structure 10 guides the moving floor 8 along a path around the treatment area 9. It forms, below the treatment area 9, a substantially horizontal planar floor surface, which serves as access service, and above said access surface. It also forms a substantially cylindrical separating wall, which surrounds the treatment area 9 as far as the first annular position α and allows a lateral axis bay 7 toward the treatment chamber 6 to remain.

The lower segment 8' of the floor 8 comprises a first end 11' connected to the irradiation unit 5 and a second end 12' passing below the floor 13 of the treatment chamber 6. This lower segment 8' can be pulled by the irradiation unit 5 from a lower docked position, in which it is found when the irradiation unit 5 is in the second angular position β, to a final operational position, in which it is found when the irradiation unit 5 is in the first angular position α, and in which it forms the substantially horizontal planar floor surface.

The upper segment 8" of the floor 8 comprises a first end 11" connected to the irradiation unit 5, opposite the first end 11' of the lower floor, and a second end 12" passing above a ceiling 14 of the treatment chamber 6. This upper segment 8" can be pulled by the irradiation unit 5 from an upper docked position, in which it is found when said irradiation unit 5 is in the first angular position α, to a final operational position, in which it is found when the irradiation unit 5 is in the second angular position β, and in which it at least partially forms the substantially horizontal planar floor surface.

The lower segment 8' and the upper segment 8" are segments with a finite length each comprising a free end 12', 12". They are preferably made up of a plurality of rigid transverse segments 15, which are articulated to each other such that the moving floor 8 can follow the curved path defined by the guide structure. It should be noted that while the lower segment 8' must be capable of serving as an access surface over nearly all of its length, only a small length of the upper segment arranged in the immediate vicinity of the irradiation unit 5 must in principle be capable of serving as an access surface, the residual length of said upper segment 8" serving solely as a substantially cylindrical separating wall, but never as an access surface. Over this residual length, the upper segment 8" can therefore have a lighter structure, as it is not required to support any load.

Figure 3:
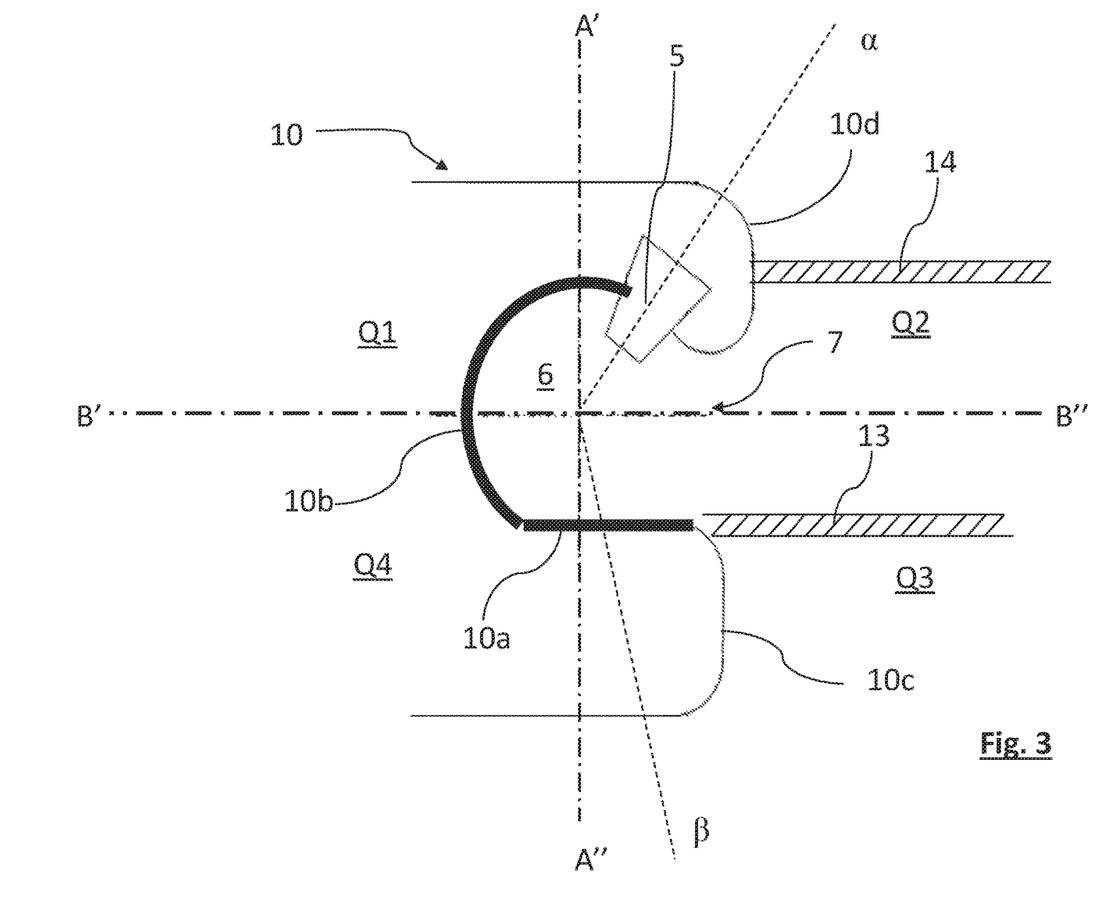
FIG. 3: is a very simplified cross-section of the hadron therapy installation according to FIG. 1, the cutting plane being perpendicular to the axis of rotation of the irradiation unit, said cross-section first and foremost conceptually showing a guide structure guiding a moving floor.

FIG. 3 diagrammatically shows the guide structure guiding the moving floor 8. The structure comprises two identical sets of guide rails 10a, 10b, 10c and 10d positioned symmetrically on either side of the passage for the irradiation unit 5 closed by the moving floor 8 (in FIG. 3, the rails of the first set hide the rails of the second set). The lower 8' and upper 8" segments are arranged slidingly in said rails 10a, 10b, 10c and 10d and can be driven by the irradiation unit 5.

In one preferred embodiment, these guide rails comprise different portions 10a, 10b, 10c and 10d to define: (1) the substantially horizontal planar floor surface below the treatment area 9; (2) the substantially cylindrical separating wall that upwardly surrounds the treatment area 9; (3) the lower docked position for the lower segment 8'; and (4) the upper docked position for the upper segment 8".

The substantially horizontal planar floor surface is defined by the first portion 10a of the rails. The latter comprises straight rails, capable of supporting and guiding the moving floor 8 along a linear path, preferably such that the substantially horizontal planar floor surface is substantially at the same level as the floor 13 of the treatment chamber 6.

The separating wall in the form of a substantially cylindrical roof is defined by a second rail portion 10b. The latter comprises rails in the shape of an arc of circle, for example an arc of circle slightly larger than 180°, as shown in FIG. 3. This second rail portion 10b extends the first portion 10a upward as far as said first angular position α, so as to guide said moving floor 8 along a path in the shape of an arc of circle around the treatment area 9, allowing a lateral axis bay 7 toward the treatment chamber 6 to remain. This lateral axis bay 7 for example makes it possible to position a robotic support 4 for a bed laterally with respect to the treatment chamber 6, as shown diagrammatically in FIG. 2.

The lower docked position is defined by a third rail portion 10c. The latter comprises a rail substantially in the shape of a capital "J" lying on its back, having a rounded branch (=lower branch of the "J") and a straight branch (=rising branch of the "J"). The end of the rounded branch is connected to the end of a straight rail of the first portion 10a and extends the latter downward. The straight branch extends below the irradiation unit 5, when the latter is in its lower position, and is preferably arranged in a substantially horizontal plane. The third rail portion 10c consequently guides the lower segment 8' along a path in the form of an open loop at least partially below the irradiation unit 5.

The upper docked position is defined by a fourth rail portion 10d. The latter comprises a rail substantially in the form of a capital "J" lying on its front, having a rounded branch (=lower branch of the "J") and a straight branch (=rising branch of the "J"). The end of the rounded branch is connected to the end of a rail in the shape of an arc of circle of the second portion 10b and extends the latter upwardly. The straight branch extends above the irradiation unit 5, when the latter is in its upper position, and is preferably arranged in a substantially horizontal plane. The fourth rail portion 10d consequently guides the upper segment 8" along a path in the form of an open loop at least partially above the irradiation unit 5.

It will be understood that the configuration of the guide rails 10 as proposed makes it possible to minimize the volume of the hadron therapy installation while ensuring relatively easy movement of the floor 8 in said guide rails 10.

The configuration of the proposed moving floor 8 requires lower 8' and upper 8" moving segments long enough to cover the entire passage irrespective of the position of the irradiation unit 5. The length of the lower 8' and upper 8" segments makes the weight of said segments relatively significant. In order to assist the irradiation unit in driving the lower 8' and upper 8" segments and in order to substantially reduce the risk of blockage of the upper segment 8", a counterweight 19 is connected to the free end 12" of the upper segment 8". This counterweight exerts, on the free end 12" of the upper segment 8", a traction force toward the upper docked position that is sufficient to keep the upper segment 8" constantly under axial tension, independently of the angular position and the direction of movement of the irradiation unit 5. At the same time, this traction unit also at least partially compensates the force exerted by the weight of the lower segment 8' on the irradiation unit and thus at least partially discharges the latter.

FIG. 2 shows that said counterweight 19 is advantageously connected to the free end 12" of the upper segment 8" using a cable 17 guided by at least one pulley 18. Such pulleys 18 (or other guide means) serve to keep the cable 17 always substantially in the axis of the rails 10d.

Figure 4A:
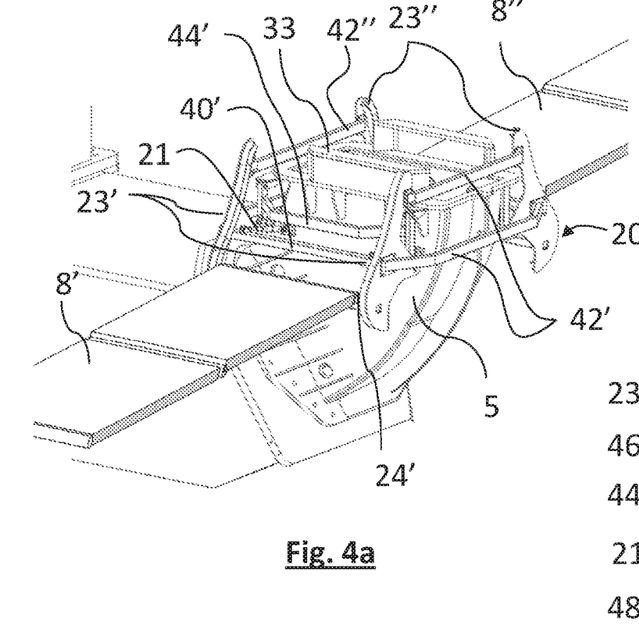
FIG. 4*a*: is a three-dimensional view of the irradiation unit and a portion of the moving floor, more precisely showing how the moving floor is connected to said irradiation unit via a traction frame.

According to one preferred embodiment, the irradiation unit 5 is surrounded by a traction frame 20 to which said lower 8' and upper 8" segments are attached, as shown in FIG. 4a. This traction frame 20 serves to transmit a traction force from the irradiation unit 5 on the lower segment 8' and the upper segment 8".

The traction frame 20 and the mechanical connection between the traction frame 20 and the irradiation unit 5 will be described in more detail in reference to FIGS. 4a, 4b and 4c. As shown in FIG. 4a, the traction frame 20 comprises a first pair of traction rails 23' for the lower segment 8' and a second pair of traction rails 23" for the upper segment 8". The traction rails 23' of the first pair are rigidly connected using at least one first crosspiece 40'. Similarly, the traction rails 23" of the second pair are rigidly connected using at least one second crosspiece, which is not visible in FIG. 4a. Lateral elements 42', 42" close the traction frame 20 around the irradiation unit 5, by rigidly interconnecting the first pair of traction rails 23' to the second pair of traction rails 23". The traction frame 20 is than a rigid frame surrounding the irradiation unit 5 with a certain functional play in both directions of movement of the irradiation unit 5.

Figure 4B:
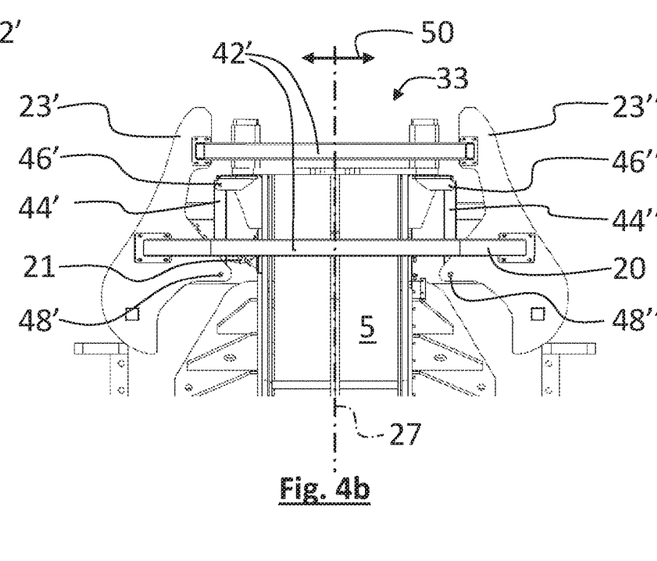
FIG. 4*b*: is a two-dimensional view used to describe the connection between the traction frame and the irradiation unit (the moving floor is not shown in this figure)

FIG. 4b shows that said traction frame 20 is supported by the irradiation unit 5 using a suspension mechanism comprising two articulated suspension arms 44' and 44". The arm 44', which is situated on the side of the first pair of traction rails 23', is connected using a first articulation 46' to the irradiation unit 5 and using a second articulation 48' to the traction frame 20, here for example to the first pair of traction rails 23'. Similarly, the arm 44", which is situated on the side of the second pair of traction rails 23", is connected using a first articulation 46" to the irradiation unit 5 and using a second articulation 48" to the traction frame 20, here for example to the second pair of traction rails 23". It will be noted that the axes of rotation of the four articulations 46', 48', 46" and 48" pass through the four corners of a parallelogram defined in a plane perpendicular to the axis of rotation 3 of the rotary gantry 2.

Figure 4C:
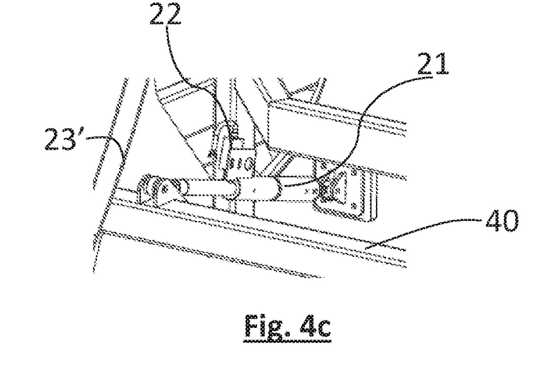
FIG. 4*c*: is an enlarged view of a portion of FIG. 4*a*.

As shown in FIG. 4c, a telescoping element 21 is connected between the irradiation unit 5 and the traction frame 20, more specifically between the irradiation unit 5 and the crosspiece 40 of the traction frame 20. This more particularly involves a telescoping element whereof the extension and shortening are, during normal operation, blocked by a stop key (not shown in FIG. 4c). When the force transmitted (depending on the direction of rotation of the irradiation unit, this may be either a traction force or a compression force) exceeds a certain threshold, said key breaks, i.e., it is for example sheared. The telescoping element 21 can then freely extend and shorten, i.e., it no longer transmits a notable force from the irradiation unit 5 to the traction frame 20.

It will be noted that it is possible to provide a single telescoping element 21, which is preferably arranged in a median plane of the traction frame 20, or a pair of telescoping elements 21, each of said telescoping elements 21 then preferably being arranged in the immediate vicinity of one of the traction rails 23, as shown in FIGS. 4a and 4c. It suffices, however, to provide that this or these telescoping element(s) 21 are on the side of the traction rails 23', or on the side of the traction rails 23".

As long as their stop key is intact, these telescoping elements 21 transmit the traction and thrust forces between the irradiation unit 5 and the traction frame 20, and keep the traction frame 20 centered relative to the irradiation unit 5. When the stop key breaks under a force exceeding said threshold value, these telescoping elements 21 can elongate (under a traction force) or shorten (under a compression force). The traction frame 20 and the irradiation unit 5 can now undergo a relative movement conditioned by the suspension mechanism of the traction frame 20 described above. It follows that if the traction frame 20 abuts against an obstacle, for example an immobilized floor, the irradiation unit 5 can continue its rotation by a certain angle; it can do so from its initial central position in both directions of rotation, as indicated by the double arrow 50 in FIG. 4b.

Reference 22 in FIG. 4c identifies a detection system 22 that is capable of detecting either a rupture of the key, or an extension or shortening of the telescoping element 21. A system signal of this detection system 22 is then used by a monitoring system to activate an emergency stop of the rotation of the irradiation unit 5.

In normal operation, traction, thrust forces, respectively, are transmitted from the irradiation unit 5 to the traction frame via the telescoping elements 21, which behave like rigid elements and keep the traction frame 20 centered relative to the irradiation unit 5. If the floor 8 becomes immobilized, the traction frame 20 is rapidly frozen, and the traction or compression force in the telescoping elements 21 subsequently increases. If said threshold value for the force to be transmitted is exceeded, the stop keys of the telescoping elements 21 break, this rupture is detected by the detection system 22, and the monitoring system activates an emergency stop of the rotation of the irradiation unit 5. Between the activation of the emergency stop of the rotation and the complete stop of the irradiation unit 5, the latter may still rotate by an angle of several degrees. Given that after ruptures of keys, the telescoping elements 21 can freely elongate or shorten, respectively, this residual rotation of the irradiation unit 5 may be absorbed as described above, owing to a rotation of the articulated arms 44' and 44' and a certain play provided between the traction frame 20 and the irradiation unit 5, from the initial central position in both directions of rotation of the irradiation unit 5.

Figure 5A:
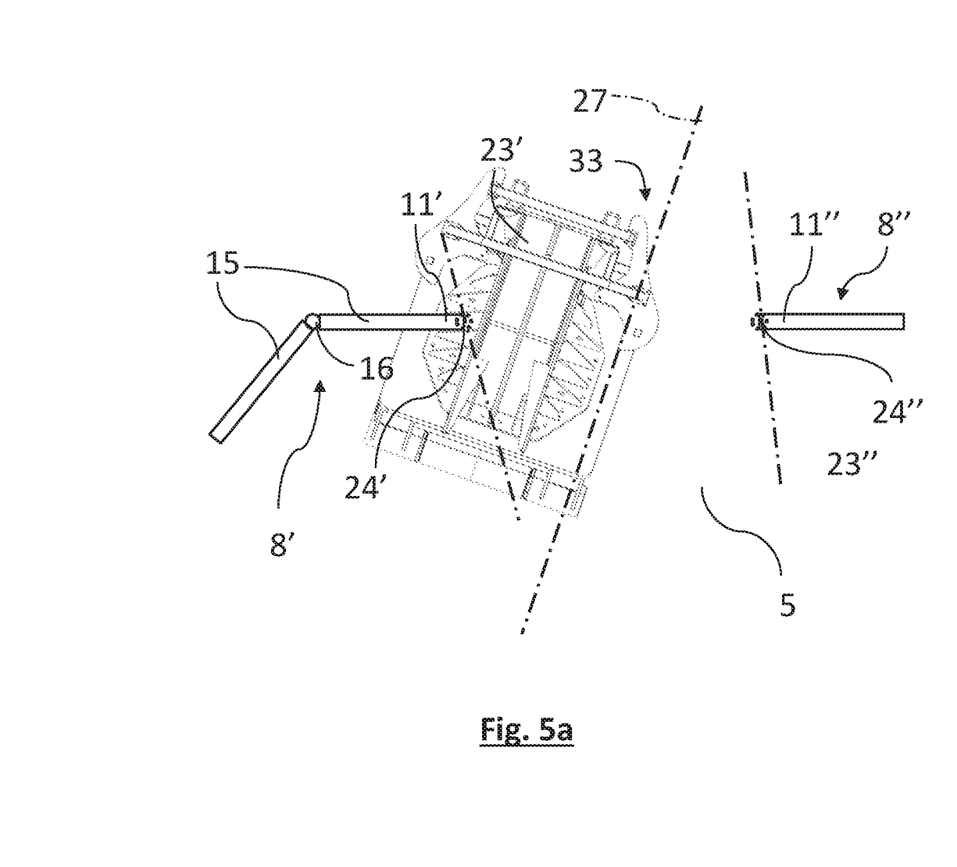
FIG. 5*a*: is a two-dimensional view of the irradiation unit and a portion of the moving floor.

As shown in FIG. 5a, the first end 11' of the lower segment 8' comprises pivot links 24' capable of sliding in the traction rails 23', and the first end 11" of the upper segment 8" comprises pivot links 24" capable of sliding in the traction rails 23".

These traction rails 23', 23" have a shape and orientation suitable for the first plate of the lower segment 8', upper segment 8", respectively, and the tangent of the rail at the pivot link to form an angle that is comprised between 45° and 135° irrespective of the position of the irradiation unit 5. The closer this angle is to 90°, the more the risk of immobilization of the lower 8' and upper 8" segments is reduced.

Figure 5B:
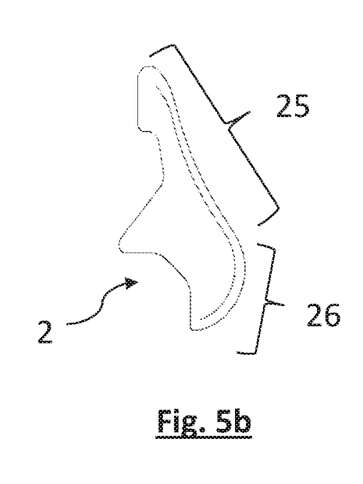
FIG. 5*b*: is an enlarged view of a traction rail of the moving floor of FIG. 5*a*.

According to one preferred embodiment as shown in FIG. 5b, the shape of the traction rails 23', 23" may be likened to the shape of a half-pear. The traction rail 23 shown in FIG. 5b thus comprises:

a first substantially linear portion 25, which, in the traction frame 20, is close to the terminal end 33 of the irradiation unit 5, forming, with the direction of the central axis 27 of the irradiation unit 5, an angle comprised between 15° and 40°; and a second curved portion 26, which, in the traction frame 20, is further from the terminal end 33 of the irradiation unit 5.

It will be noted that FIG. 5a shows the irradiation unit 5 in an extreme angular position β. In the vicinity of this extreme angular position β, the pivot links 24" of the upper segment 8" are found in the substantially linear portions 25 of the traction rails 23", and the pivot links 24' of the lower segment 8' are found in the curved portions 26 of the traction rails 23', which makes it possible to maintain an angle between the first plate of the lower segment 8' and the tangent of the traction rail 23' at the pivot links 24' comprised between 45° and 135°. In this way, when the gantry is actuated to move the radiation unit 5 from the second angular position β toward the first angular position α, the driving of the lower segment 8' is facilitated as a result.

In the vicinity of the extreme angular position α (not shown), the pivot links 24" of the upper segment 8" are found in the curved portions 26 of the traction rails 23", and the pivot links 24' of the lower segment 8' are found in the substantially linear portions 25 of the traction rails 23', which makes it possible to maintain an angle between the first plate of the upper segment 8" and the tangent of the traction rail 23" at the pivot links 24" comprised between 45° and 135°. In this way, when the gantry is actuated to move the irradiation unit 5 from the first angular position α toward the second angular position β, the driving of the upper segment 8" is facilitated as a result. At a certain distance of the extreme angular positions α and β of the radiation unit 5, the pivot links 24', 24" slide primarily in the first substantially linear portion 25 of the traction rails 23', 23".

Figure 6:
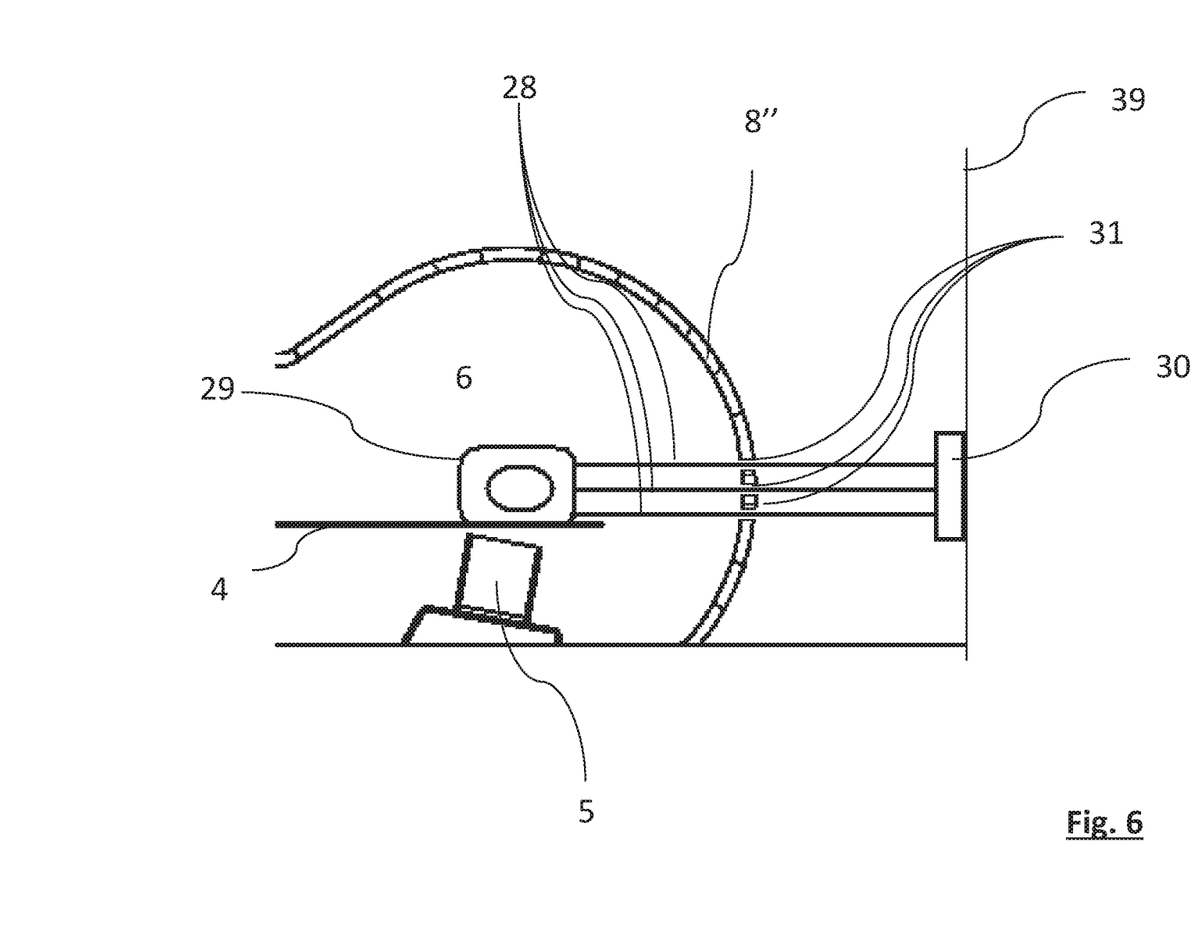
FIG. 6: is a very simplified cross-section of the hadron therapy installation of FIG. 1, the cutting plane being perpendicular to the axis of rotation of the irradiation unit, diagrammatically showing the integration into said hadron therapy installation of a laser device for positioning a patient.

According to one preferred embodiment, as shown in FIG. 6, the hadron therapy insulation comprises a source 30 capable of producing a laser beam 28 for positioning a patient 29. The source 30 is for example a wall, behind the moving floor 8, that forms the cylindrical wall of the treatment chamber 6. At least one of the plates of the floor 8 comprises an opening 31 for the passage of the laser beam 28. Preferably, at least two laser sources are used and at least three openings are formed in the moving floor 8 to project a flared laser beam over a height of approximately 50 cm on the patient 29.

Figure 7:
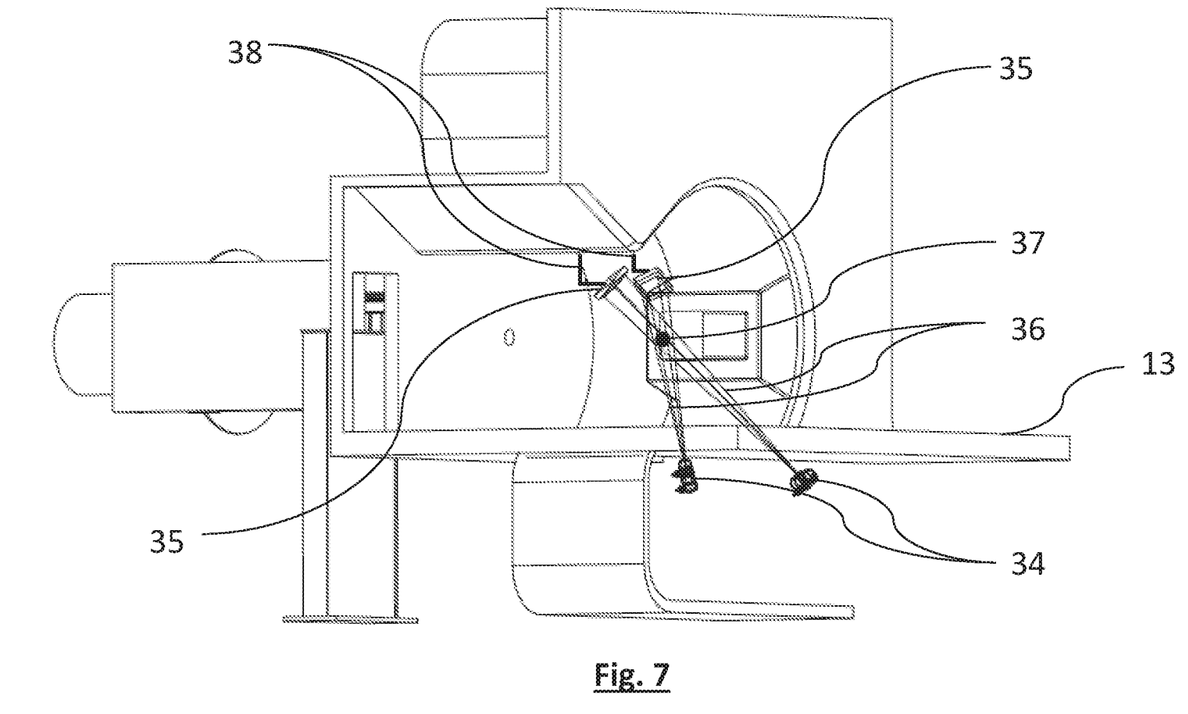
FIG. 7: is a three-dimensional view of a hadron therapy installation as in FIG. 1, further comprising an imaging device.

Still according to a preferred embodiment of the invention, as shown in FIG. 7, the hadron therapy installation comprises a stationary imaging device 34, 35 for precise positioning of the patient 29 after pre-positioning using said laser beam 28. The imaging device preferably comprises two x-ray tubes 34 situated below the floor 8 and two x-ray detection panels 35 situated in the treatment chamber 6. The fixed imaging device makes it possible to position the patient precisely after pre-positioning using lasers.

Preferably, the x-ray tubes 34 and the detection panels 36 are oriented such that the produced x-ray beams 36 intersect at the isocenter 37 of the rotary gantry 2. Preferably, two x-ray tubes 34 are situated in the ground, on a first side of the moving floor 8, and two detection panels 35 are suspended from the ceiling by supports 38, on the other side of the moving floor as shown in FIG. 7. It is also possible to design a configuration of the imaging device in which an x-ray tube 34 and a detection panel 35 are situated on each side of the moving floor 8. The positioning of this imaging device makes it possible to take slides for a plurality of angular positions assumed by the irradiation unit. One skilled in the art may conceive a particular arrangement of the x-ray tubes and the detection panels so as to image both intracranial areas of a patient and pelvic areas.

| List of references | |
|---|---|
| 1 | hadron therapy installation |
| 2 | rotary gantry |
| 3 | horizontal axis of rotation |
| 4 | robotic support for a bed |
| 5 | irradiation unit |
| 6 | treatment chamber |
| 7 | lateral access bay to 6 |
| 8 | moving floor |
| 8' | lower segment of 8 |
| 8" | upper segment of 8 |
| 9 | treatment area |

| List of references | |
|---|---|
| 10 | guide structure |
| 10a | first rail portion |
| 10b | second rail portion |
| 10c | third rail portion |
| 10d | fourth rail portion |
| 11' | first end of 8' |
| 11" | first end of 8" |
| 12' | second end of 8' |
| 12' | second end of 8" |
| 13 | floor of 6 |
| 14 | ceiling of 6 |
| 15 | articulated segment of 8 |
| 17 | cable |
| 18 | pulley |
| 19 | counterweight |
| 20 | traction frame |
| 21 | piston |
| 22 | load cell |
| 23' | pair of traction rails of 8' |
| 23" | pair of traction rails of 8" |
| 24' | pivot link of 8' |
| 24" | pivot link of 8" |
| 25 | first (linear) portion of 23', 23" |
| 26 | second (curved) portion of 23', 23" |
| 27 | central axis of 5 |
| 28 | laser beam |
| 29 | patient |
| 30 | laser source |
| 31 | opening in 8 |
| 33 | terminal end of 5 |
| 34 | XR tube |
| 35 | XR detection panel |
| 36 | XR beam |
| 37 | isocenter |
| 38 | suspension supports of 35 |
| 39 | support for 30 |
| 40' | crosspiece of 20 |
| 42', 42" | lateral elements of 20 |
| 44', 44" | articulated suspension arms |
| 46', 46" | articulation between 44', 44" and 5 |
| 48', 48" | articulation between 44', 44" and 23', 23" |
| 50 | bend |

The invention claimed is:

1. A hadron therapy installation comprising:
an irradiation unit with a horizontal axis of rotation, wherein the irradiation unit is configured to rotate around a treatment area between a first angular position (α), situated above the treatment area, and a second angular position (β), situated below the treatment area;
a moveable floor wherein the moveable floor further comprises a band deformable in a longitudinal direction, wherein the band has a lower segment and an upper segment respectively situated on either side of the irradiation unit;
a guide assembly for guiding the movable floor along a path around the treatment area such that the movable floor forms a substantially horizontal floor surface below the treatment area and a wall surrounding the treatment area up to the first angular position (α) above the floor surface;
the lower segment is configured to be pulled by the irradiation unit from a lower docked position, corresponding to when the irradiation unit is in the second angular position (β), to a final operational position, corresponding to when the irradiation unit is in the first angular position (α) and in which the lower segment at least partially forms the substantially horizontal floor surface; and
the upper segment is configured to be pulled by the irradiation unit from an upper docked position, corresponding to when the irradiation unit is in the first angular position (α), to a final operational position, corresponding to when the irradiation unit is in the second angular position (β) and in which the upper segment at least partially forms the substantially horizontal floor surface;

wherein the lower segment and the upper segment each comprise a free end; and wherein a traction device comprising a counterweight is connected to the free end of the upper segment, so as to exert a traction force on the upper segment toward the upper docked position sufficient to keep the upper segment under axial tension independent from the first and second angular positions and direction of movement of the irradiation unit.

2. The installation according to claim 1, wherein the counterweight is connected to the free end of the upper segment by at least one cable guided by at least one pulley.

3. The installation according to claim 2, wherein the end portion of the upper segment is arranged above the irradiation unit when the upper segment is completely arranged in said upper docked position.

4. The installation according to claim 3, wherein in the upper docked position, the upper segment advantageously forms an open loop, and the end portion of the upper segment is arranged in a plane extending above the irradiation unit.

5. The installation according to claim 4, wherein an end portion of the lower segment is arranged below the irradiation unit when the lower segment is arranged in the lower docked position.

6. The installation according to claim 5, wherein in the lower docked position, the lower segment forms an open loop, and the end portion of the lower segment is arranged in a plane extending below the irradiation unit.

7. The installation according to claim 6, further comprising guide rails comprising:
a first portion, configured to guide the moveable floor along a linear path to form the substantially horizontal floor surface below the treatment area;
a second portion configured to guide the moveable floor along a path in the shape of an a circular arc to form, above the substantially horizontal floor surface, a surface in the shape of a cylinder segment that surrounds the treatment area up to the first angular position (α);
a third portion, which extends the first portion downward, and is configured to guide the lower segment along a path in the form of an open loop to form the lower docked position for the lower segment; and
a fourth portion, which extends the second portion upward, which is configured to guide the lower segment along a path in the shape of an open loop, to form the upper docked position for the upper segment.

8. The installation according to claim 7, further comprising:
a rigid traction frame surrounding the irradiation unit with functional play on either side thereof, wherein the traction frame is configured to be supported by the irradiation unit such that the irradiation unit in rotation can move relative to the traction frame within a limit of the functional play;
the segments of the floor are connected on either side of the rigid traction frame; and
a piston is arranged between the traction frame and the irradiation unit so as to immobilize the traction frame in a central position relative to the irradiation unit, as long as the force transmitted by the piston remains below a threshold value, wherein the piston comprises at least one safety element that gives way when the transmitted force exceeds the threshold value, allowing relative movement of the irradiation unit with respect to the traction frame while taking advantage of the functional play.

9. The installation according to claim 8, further comprising:
a detection device configured to detect that the at least one safety element has given way; and
a monitoring system configured to activate an emergency stop of the rotation of the irradiation unit when the said detection device detects that the at least one safety element has given way.

10. The installation according to claim 9, wherein the traction frame is supported by the irradiation unit by means of two suspension arms, so as to form a mechanism with four articulations arranged at the four corners of a parallelogram.

11. The installation according to claim 10, wherein:
the piston comprises at least one telescoping element, an extension and shortening of which are blocked by at least one stop key, which forms the at least one safety element, which gives way when the transmitted force exceeds the threshold value.

12. The installation according to claim 8, wherein a connection between the irradiation unit and the lower segment comprises a first pivot joint and a first traction rail, wherein the first traction rail is configured to guide the first pivot joint along a trajectory defined to optimize the transmission of a traction force from the irradiation unit on the lower segment, wherein a connection between the irradiation unit and the upper segment comprises a second pivot joint and a second traction rail, and wherein the second traction rail is configured to guide the second pivot joint along a trajectory defined to optimize the transmission of a traction force from the irradiation unit on the upper segment.

13. The installation according to claim 12, wherein the first and second traction rails define:
a substantially linear trajectory portion; and
a rounded convex trajectory portion following said substantially linear trajectory portion.

14. The installation according to claim 13, further comprising a laser source configured to produce a laser beam for positioning a patient, the laser source configured to be positioned on a support behind the moveable floor, and wherein at least one of the lower and upper segments comprises an opening for the passage of the laser beam.

15. The installation according to claim 14, further comprising an imaging device situated on either side of the moveable floor and the imaging device comprising at least one x-ray tube and an x-ray detection panel.

16. The installation according to claim 15, wherein the moveable floor comprises a plurality of transverse segments that are articulated to each other such that the moveable floor can follow the path defined by the guide rails.

17. The installation according to claim 16, wherein:
when four quadrants defined by a horizontal plane (B', B") and a vertical plane (A', A") both containing an axis of rotation (S) are numbered as follows:
the first and second quadrants are located next to one another above the horizontal plane (B'>B");
the third quadrant is located below the second quadrant; and
the fourth quadrant is located below the first quadrant;
in the said first angular position (α), the irradiation unit is arranged in said first quadrant; and in the its second angular position (β), the said-irradiation unit is arranged either at a boundary of the third and fourth quadrants, or in the fourth quadrant.

18. A hadron therapy installation (4) comprising:
an irradiation unit with a horizontal axis of rotation, wherein the irradiation unit is configured to rotate around a treatment area;
a moveable floor comprising a band deformable in a the longitudinal direction and guided in a guide assembly, the moveable floor further comprising a segment on either side of the irradiation unit; and
a traction mechanism arranged between the irradiation unit and the said two segments of the moveable floor, such that the irradiation unit can drive said floor segments via the traction mechanism that rotates about the axis of rotation;
wherein the traction mechanism comprises:
a rigid traction frame surrounding the irradiation unit with functional play on either side thereof and supported by the irradiation unit such that the rotating irradiation unit in rotation can move relative to the traction frame within limits of said functional play wherein the segments of the floor are connected on either side of the rigid traction frame; and
a piston arranged between the traction frame and the irradiation unit so as to freeze the traction frame in a central position relative to the irradiation unit, as long as the force transmitted by the piston remains below a threshold value, wherein the piston comprises at least one safety element that gives way when the transmitted force exceeds the threshold value to allow a relative movement of the irradiation unit with respect to the traction frame while taking advantage of the functional play.

19. The installation according to claim 18, further comprising:
a detection device configured to detect that the at least one said safety element has given way; and
a monitoring system configured to activate an emergency stop of the rotation of the irradiation unit when the detection device detects that the at least one safety element has given way.

20. The installation according to 19, wherein the traction frame is supported by the irradiation unit by means of two suspension arms so as to form a mechanism with four articulations arranged in the four corners of a parallelogram.

21. The installation according to 20, wherein:
the piston further comprises at least one telescoping element, wherein an extension and shortening of the at least one telescoping element are blocked by at least one stop key, wherein the at least one stop key forms the at least one safety element and gives way when the transmitted force exceeds the threshold value.

22. The installation according to claim 21, wherein:
the traction frame comprises, for each floor segment, at least one traction rail to which one end of the lower and upper floor segments is connected using a pivot joint, wherein the at least one traction rail guiding the pivot joint along a trajectory is configured to optimize the transmission of a traction force from the traction frame on each floor segment.

23. The installation according to claim 22, wherein the traction rail comprises:
a substantially linear trajectory portion; and
a rounded convex trajectory portion.

* * * * *